US00PP14929P2

(12) United States Plant Patent
Strope

(10) Patent No.: US PP14,929 P2
(45) Date of Patent: Jun. 22, 2004

(54) PETUNIA PLANT NAMED 'BALRUFWHIT'

(50) Latin Name: *Petunia×hybrida*
Varietal Denomination: Balrufwhit

(75) Inventor: Kerry M. Strope, Pismo Beach, CA (US)

(73) Assignee: Ball Floraplant, a division of Ball Horticultural, West Chicago, IL (US)

( * ) Notice: Subject to any disclaimer, the term of this patent is extended or adjusted under 35 U.S.C. 154(b) by 84 days.

(21) Appl. No.: 10/107,711

(22) Filed: Mar. 26, 2002

(51) Int. Cl.[7] ..... A01H 5/08
(52) U.S. Cl. ..... Plt./356
(58) Field of Search ..... Plt./356

*Primary Examiner*—Bruce R. Campell
*Assistant Examiner*—Michelle Kizilkaya
(74) *Attorney, Agent, or Firm*—Wood, Phillips, Katz, Clark & Mortimer

(57) ABSTRACT

A new and distinct Petunia plant named 'Balrufwhit', characterized by its fully double white flowers, upright, mounded-trailing habit, and dark green leaves.

2 Drawing Sheets

Latin name of the genus and species of plant claimed: *Petunia×hybrida*
Variety denomination: 'Balrufwhit'

BACKGROUND OF THE INVENTION

The present invention comprises a new and distinct Double Petunia plant, botanically known as *Petunia×hybrida*, and hereinafter referred to by the cultivar name 'Balrufwhit'.

'Balrufwhit' is the result of a planned breeding program with the objective of developing Petunia cultivars with large, double flowers and vigorous mounded-trailing growth habits.

The female parent of 'Balrufwhit' was the proprietary *Petunia×hybrida* variety, designated 'BFP-39' (not patented), which exhibits a vigorous trailing habit and single white flowers. The male parent of 'Balrufwhit' was the proprietary *Petunia×hybrida* variety, designated 'BFP-61' (not patented), which exhibits an upright habit and double white flowers. The new cultivar was discovered and selected as a single seedling originating from the above stated cross during November 1998 in a controlled environment at Arroyo Grande, Calif. and initially designated 'BFP-740'.

Asexual reproduction of the new cultivar has been carried out at Arroyo Grande, Calif. and West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits fully double white flowers;

(b) forms dark green foliage;

(c) exhibits a good basal branching character; and (d) exhibits an upright, mounded-trailing growth habit.

The new cultivar of the present invention can be compared to Petunia plant named 'Cobink' (U.S. Plant Pat. No. 12,012) and 'Cascadia Double Pink' (not patented). However, in side-by-side comparisons, plants of the new cultivar have larger sepals and larger flowers with more petals of a different color than 'Cobink'. 'Balrufwhit' has larger flowers, larger sepals and lighter colored flowers than either 'Cobink' or 'Cascadia Double Pink'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 12 weeks in a greenhouse at West Chicago, Ill., U.S.A.

DETAILED BOTANICAL DESCRIPTION

The cultivar 'Balrufwhit' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Oct. 15, 2001. The readings were taken between 1:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double poly carbonate covered greenhouse under conditions comparable to those used in commercial practice. A soilless growth medium was utilized while temperatures of approximately 55° to 75° F. (13° to 24° C.) during the day and approximately 50° to 60° F. (10° to 16° C.) during the night and light levels of 5,000 to 8,000 footcandles were maintained.

Classification:

*Botanical.*—*Petunia×hybrida* cultivar 'Balrufwhit'.

Parentage:

*Female parent.*—Proprietary *Petunia×hybrida* variety designated 'BFP-39'.

*Male parent.*—Proprietary *Petunia×hybrida* variety designated 'BFP-61'.

Propagation:

*Type cutting.*—Terminal tip.

*Time to initiate roots.*—Approximately 7 to 10 days.

*Time to develop roots.*—Approximately 21 to 30 days.

*Root description.*—Fibrous, branching.

Plant description:

*Crop time.*—Approximately 6 to 8 weeks are required to produce a finished plant from rooted cuttings.

*Habit of growth.*—Moderately vigorous with good basal branching. Pinching improves basal branching.

*Form.*—Upright, mounded-trailing.

*Plant height.*—A mature plant, 12 weeks after the planting of a rooted cutting, commonly measures approximately 21.3 cm from the soil line to the top of the plant plane.

*Plant spread.*—Approximately 37.4 cm.

*Lateral branches.*—An average of 4 branches per plant, approximately 31.2 cm in length and 3 mm in diameter, densely pubescent and 144A in color. Internode length at the middle of the branch is approximately 3.1 cm.

*Foliage.*—Leaves are non-fragrant, single, arrangement is alternate along the stem becoming opposite at the base of the peduncle. Leaves are ovate with entire margin, acute apex, attenuate base and are at an acute angle to the stem. Upper and lower surfaces are densely pubescent, sticky and slightly rugose. The leaf margin is densely pubescent. There are approximately 16 leaves per branch. Leaf length is approximately 5.4 cm and width is approximately 3.1 cm. The upper surface of young foliage is slightly darker than 144A and the lower surface is 144A. The upper surface of mature foliage is more yellow than 137A and the lower surface is more yellow than 137C. Both upper and lower surfaces have pinnate venation closest to 144B. The petiole length is approximately 4 mm, the diameter is approximately 3 mm and the color is closest to 144C.

Flowering description:

*Flowering habit.*—Freely flowering.

*Natural flowering season.*—Year round in greenhouse environment and from spring through fall in outdoor garden.

*Lastingness of the bloom.*—Bloom remains open for approximately 5–7 days.

Flower description:

*Type.*—Double, solitary, axillary, salverform, with no fragrance. Flowers are persistent.

*Size.*—Length (height) is approximately 5.2 cm and diameter is approximately 8.2 cm.

*Corolla.*—Thirteen (13) obovate petals with the outer whorl of five petals fused to form corolla tube. All petals have rounded apex, entire, undulate margin and dull, smooth texture. Petal length from the throat is 3.3 cm and width at widest point is 2.8 cm. Color of upper surface is closest to 155D with venation of 144B. Color of lower surface of petals is 155D with midvein of 144B.

*Corolla tube.*—Length is approximately 2.8 cm, diameter at distal end is approximately 6 mm and diameter at proximal end is approximately 2.4 cm. Color of outer surface is 144C with venation of 144B. Color of inner surface is 145C, with venation of 144B. Outer surface is moderately pubescent and inner surface is smooth.

*Peduncle.*—Densely pubescent, at an acute angle to the stem, approximately 4.9 cm in length and 2 mm in diameter. Peduncle color is 144B.

*Flower bud.*—Ovate, elongating as it matures, approximately 2.3 cm in length and 1.8 cm in diameter at first color. Color is 144C.

*Sepals.*—Five, non-imbricate, approximately 3.2 cm in length, 1.1 cm in width, spatulate in shape with rounded apex and entire, slightly undulate margin. Both surfaces are densely pubescent. The color of the upper surface is 144A and the lower surface is darker than 144A.

*Reproductive organs.*—Stamen number is approximately 11. Anther shape is oval, color is 159B and length is approximately 2 mm. Pollen is abundant and color is 159C. The single pistil is approximately 1 cm in lenth. Stigma is funnel shaped and the color is between 145B and 145C. Style is 4 mm in length and 145C. Ovary size is 3 mm and the color is 150A.

Seed production: Seed production has not been observed.

Disease resistance: Resistance to pathogens has not been observed.

I claim:

1. A new and distinct cultivar of Petunia plant named 'Balrufwhit' substantially as herein shown and described, which:

(a) exhibits fully double white flowers;

(b) dark green foliage;

(c) a good basal branching character; and (d) an upright, mounded-trailing growth habit.

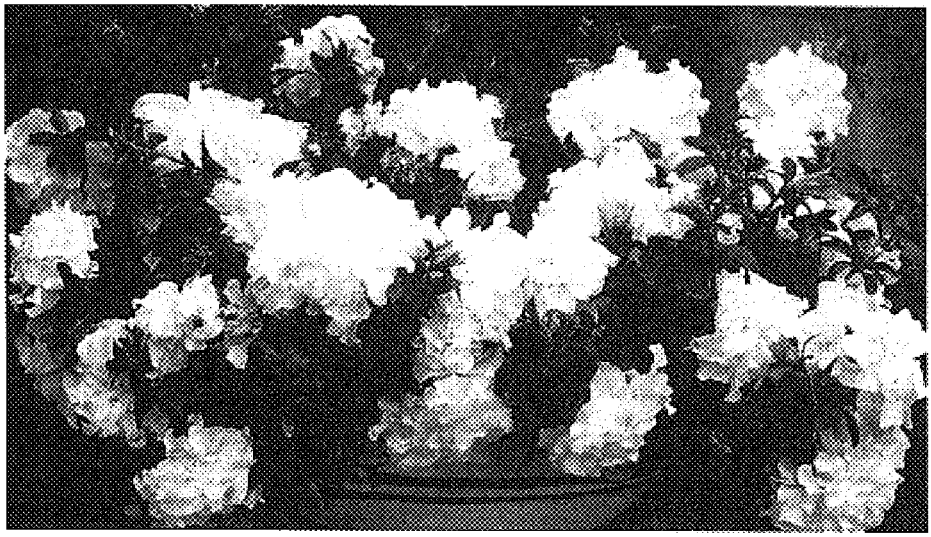

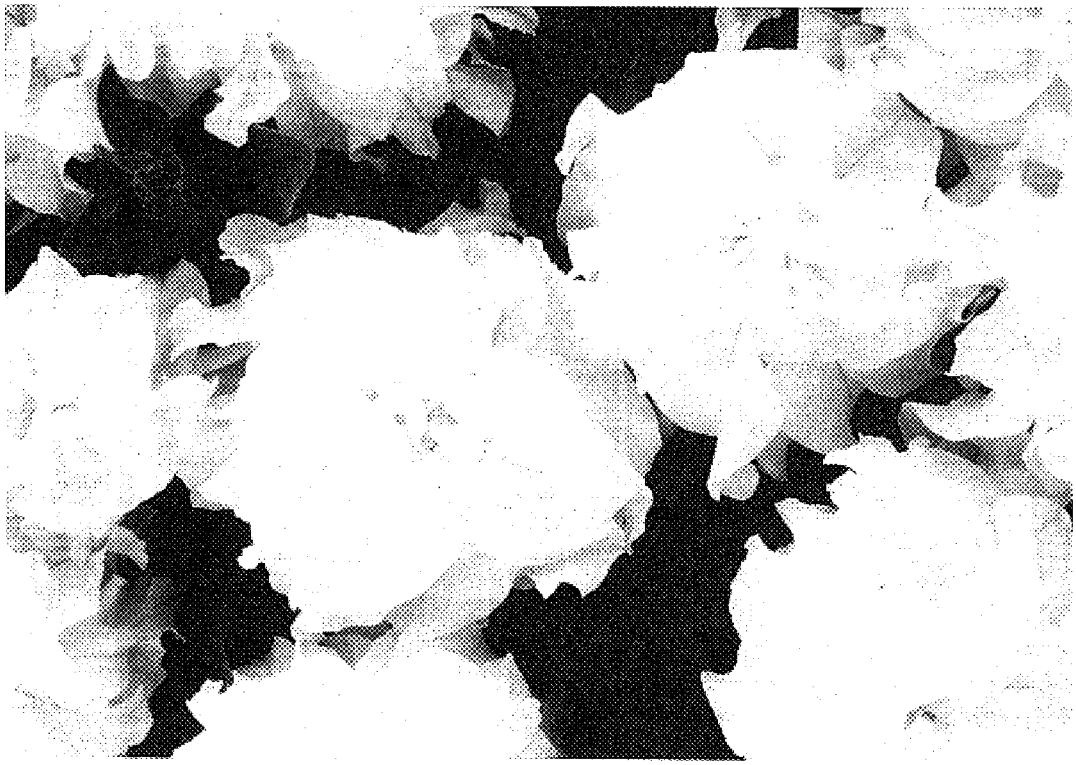

* * * * *